United States Patent
Akimoto et al.

(10) Patent No.: US 7,709,236 B2
(45) Date of Patent: May 4, 2010

(54) PROCESS FOR PRODUCING MICROBIAL FAT OR OIL HAVING LOWERED UNSAPONIFIABLE MATTER CONTENT AND SAID FAT OR OIL

(75) Inventors: Kengo Akimoto, Osaka (JP); Kenichi Higashiyama, Kobe (JP); Hiroshi Kawashima, Takatsuki (JP); Motoo Sumida, Uji (JP)

(73) Assignee: Nippon Suisan Kaisha, Ltd., Chiyoda-ku, Tokyo (JP)

( * ) Notice: Subject to any disclaimer, the term of this patent is extended or adjusted under 35 U.S.C. 154(b) by 995 days.

(21) Appl. No.: 10/530,747

(22) PCT Filed: Oct. 9, 2003

(86) PCT No.: PCT/JP03/13000

§ 371 (c)(1),
(2), (4) Date: May 2, 2005

(87) PCT Pub. No.: WO2004/033698

PCT Pub. Date: Apr. 22, 2004

(65) Prior Publication Data

US 2005/0287651 A1   Dec. 29, 2005

(30) Foreign Application Priority Data

Oct. 11, 2002   (JP) .............................. 2002-299199

(51) Int. Cl.
*C12P 7/64*   (2006.01)

(52) U.S. Cl. ...................................... 435/134
(58) Field of Classification Search .................. 435/134
See application file for complete search history.

(56) References Cited

U.S. PATENT DOCUMENTS

| | | | | |
|---|---|---|---|---|
| 5,322,780 A | * | 6/1994 | Kawashima et al. | ........ 435/134 |
| 6,117,905 A | * | 9/2000 | Higashiyama et al. | ...... 514/560 |
| 6,280,982 B1 | * | 8/2001 | Kawashima et al. | ........ 435/134 |

FOREIGN PATENT DOCUMENTS

| | | |
|---|---|---|
| CN | 1232507 A | 10/1999 |
| EP | 0 535 939 A1 | 4/1993 |
| EP | 0 535 940 A1 | 4/1993 |
| EP | 0 956 774 A1 | 11/1999 |
| EP | 0 957 173 A1 | 11/1999 |
| EP | 0957173 B1 | 11/1999 |
| EP | 000957173 B1 * | 9/2004 |
| JP | 04-341188 | 11/1992 |
| JP | 06-105680 | 4/1994 |
| JP | 6 153970 | 6/1994 |
| JP | 09-220457 | 8/1997 |
| JP | 10-191886 | 7/1998 |

OTHER PUBLICATIONS

Wang Zhiming, "Production and Application of Arachidonic acid", China Food Additives, 2001, No. pp. 30-33 (English Translation attached).

Stanbury et al., "Division of Biological and Environmental Sciences," Sep. 1, 1998, pp. 120-121.

Murakami et al., "Scale-Up of Fermenter: Survey of Industrial Fermenter Specifications," Reviews of Chemical Engineering Reports, vol. 26, No. 4 (2000) pp. 557-562 (English Abstract).

Higashiyama et al., "Culture Engineering Study of Arachidonic Acid Production by Mortierella alpina," Doctorate Thesis, Osaka University 2000.

* cited by examiner

*Primary Examiner*—Deborah D Carr
(74) *Attorney, Agent, or Firm*—Drinker Biddle & Reath LLP

(57) ABSTRACT

A process for producing a crude oil having lowered unsaponifiable matter content and/or ester-type sterol content and comprising a highly unsaturated fatty acid as a constituent fatty acid, characterized in that a microorganism capable of producing a fat or oil comprising an unsaturated fatty acid as a constituent fatty acid is cultured in a medium containing a nitrogen source concentration of 2 to 15% within a culture tank equipped with an agitation impeller satisfying the requirement that the ratio of the diameter of agitation impeller (=d) to the inner diameter of the culture tank (=D) is $d/D=0.30$ to 0.6.

20 Claims, No Drawings

PROCESS FOR PRODUCING MICROBIAL FAT OR OIL HAVING LOWERED UNSAPONIFIABLE MATTER CONTENT AND SAID FAT OR OIL

TECHNICAL FIELD

The present invention relates to a crude oil having lowered unsaponifiable matter content and/or ester-type sterol content and comprising a highly unsaturated fatty acid as a constituent fatty acid, a production process of a refined fat or oil, and said fat or oil (crude oil or refined fat or oil) and foods and drinks, therapeutic nutrition foods, animal foods, and pharmaceutical preparations with the fat or oil (crude oil or refined fat or oil) incorporated therein. In the present invention, the "unsaponifiable matter" and "ester-type sterol" refer to those extracted from microorganisms. Therefore, the "unsaponifiable matter" and "ester-type sterol" referred to in the present invention exclude any unsaponifiable matter and ester-type sterol added to the crude oil after extraction.

BACKGROUND ART

Regarding biosynthesis of human highly unsaturated fatty acids (hereinafter referred to as "PUFA"), there are two typical series, ω3 and ω6 series. ω (omega) refers to the number of carbon atoms from the terminal methyl group of the fatty acid to the carbon atom at which the first double bond is located. For example, in the case of the ω6 series, linoleic acid (18:2 ω6) is repeatedly subjected to unsaturation and carbon chain length extension and consequently converted to γ-linolenic acid (18:3 ω6), dihomo-γ-linolenic acid (20:3 ω6), arachidonic acid (20:4 ω6), and 4,7,10,13,16-docosapentaenoic acid (22:5 ω6).

Likewise, in the case of the ω3 series, α-linolenic acid (18:3 ω3) is repeatedly subjected to unsaturation and carbon chain length extension and consequently is converted to eicosapentaenoic acid (20:5 ω3), 7,10,13,16,19-docosapentaenoic acid (22:5 ω3) and 4,7,10,13,16,19-docosahexaenoic acid (22:6 ω3). Eicosapentaenoic acid (hereinafter referred to as "EPA" and docosahexaenoic acid (hereinafter referred to as "DHA") as PUFAs of the ω3 series are known to have many physiological functions, particularly prophylactic effects for lifestyle diseases, such as arterial sclerosis and thrombosis, and carcinostatic action and learning ability enhancing action, and various attempts have been made to apply these PUFAs to pharmaceutical preparations and specific food products for health care. In recent years, however, attention has also been drawn to physiological functions of PUFAs other than the ω3 series (ω6 and ω9 series).

About 10% of fatty acids constituting important organs such as blood and liver is accounted for by arachidonic acid. For example, fatty acids in phospholipids of human blood have a composition comprising 11% of arachidonic acid, 1% of eicosapentaenoic acid, and 3% of docosahexaenoic acid. The arachidonic acid is involved, as a major constituent component of a cell membrane, in the regulation of flow in the membrane to exhibit various functions in metabolism in the body and, further, plays an important role as a direct precursor of prostaglandins.

In particular, the arachidonic acid has recently drawn attention as a nutrient for infants and as a constituent fatty acid of endogenous cannabinoid (2-arachidonoyl monoglycerol, anandamide) having a nerve activating action. In general, upon ingestion of a food rich in linoleic acid, linoleic acid is converted to arachidonic acid. In patients suffering from lifestyle diseases and a reserve group of lifestyle diseases, infants, and aged persons, however, the function of enzyme involved in the biosynthesis is lowered. Therefore, the amount of arachidonic acid is likely to be deficient. For this reason, it is desirable to ingest the arachidonic acid directly as a fat or oil (constituent fatty acid of triglyceride).

For EPA and DHA as PUFAs of the ω3 series, there is fish oil as an abundant supply source. On the other hand, γ-linolenic acid, dihomo-γ-linoleinic acid, arachidonic acid, and 4,7,10,13,16-docosapentaenoic acid (22:5 ω6) as PUFAs of ω6 series are hardly obtained from conventional fat or oil supply sources, and, at the present time, fat or oil (triglycerides) comprising, as a constituent fatty acid, PUFAs produced by fermentation of microorganisms are generally used. For example, a method has been proposed wherein a fat or oil (triglyceride) comprising arachidonic acid as a constituent fatty acid is produced by culturing various microorganisms capable of producing fat or oil (triglycerides) comprising arachidonic acid as a constituent fatty acid.

Among others, the production of fat or oil containing a high arachidonic acid content (triglycerides) by using particularly microorganisms belonging to the genus *Mortierella* is known (Japanese Unexamined Patent Publication (Kokai) Nos. 63 (1988)-44891 and 63 (1988)-12290). Based on many test results, these fat or oil are said to be safe. As, however, this fat or oil is derived from microorganisms, there is no satisfactory experiences in ingestion. Therefore, at the present time, the fat or oil in question have not yet satisfactorily infiltrated into the society. On the other hand, fat or oil (triglycerides) comprising, as a constituent fatty acid, arachidonic acid produced by fermentation have begun to be used in applications where arachidonic acid should be used, for example, in the field of infant nutrition and, specifically, in infant formula.

The fat or oil produced from naturally occurring products such as animals and plants are subjected to refining processes, such as degumming, deoxidation, deodorization, decoloration, molecular distillation, and wintering and are then put on the market as edible fat or oil. For example, fat or oil obtained by squeezing from oil plants contain a large amount of impurities and thus as such cannot be used as edible fat or oil. Except for sesame oils and olive oils which have often been eaten, these fat or oil are generally refined before use as edible oils.

For example, in the degumming process, phospholipids, carbohydrates, resins, protein compounds, trace metals, and coloring matter contained in unrefined oils are removed. In the deoxidation (alkali refining) process, fatty acids, coloring matter, phospholipids, trace metals, sulfur compounds, oil insolubles, and oxidation products are removed. In the decoloration process, coloring matter, gummy matter, trace metals, soap components, oxidation products, and phospholipids are removed. In the deodorization process, fatty acids, monoglycerides, diglycerides, aldehydes, alcohols, ketones, hydrocarbons, coloring matter, sulfur compounds, peroxides, oxidative degradation products and other odor components are removed.

Fat or oil contain organic compounds, which are soluble in oils and are less likely to be degraded with an alkali, called "unsaponifiable matter." For example, compounds such as higher alcohols, sterols, hydrocarbons, tocopherols and carotenoids are known as constituent components of unsaponifiable matter. In the fat or oil refining processes, unsaponifiable matter contents can be reduced but cannot be fully removed. Sterols are known to exist as main components of unsaponifiable matter in fat or oil produced by microorganisms.

Sterols present in fat or oil are divided into free types and ester types. In the refining processes, the free type can be removed, but on the other hand, the ester type can hardly be removed. For example, after degumming, deoxidation, decoloration, and deodorization processes, the contents of the sterol content (mg/g) of soybean oil are 3.4, 3.0, 2.0, and 1.6, respectively, for the free type, and is 0.6, 0.6, 0.6, and 0.6, respectively, for the ester type ("Shokuyo Yushi no Kagaku (Science of edible fat or oil)," pp. 20-21, SAIWAISHOBO).

As irremovable sterols and the like are contained as a part of unsaponifiable matter, in general, the unsaponifiable matter content is extensively used as an index of the quality of refined fat or oil or as a control index of the refining process. For example, according to Japanese Agricultural Standards, the content of unsaponifiable matter, e.g., in edible safflower oils, edible soybean oils, and edible palm oils should be not more than 1.0% (the 523rd notification (Mar. 31, 1969) of the Ministry of Agriculture, Forestry and Fisheries). For infants, cholesterol is necessary, and an infant formula having an increased cholesterol content is on the market. Plant-derived sterols are contained in vegetable edible fat or oil. The presence of the vegetable-derived sterols disadvantageously inhibits cholesterol absorption in infants (Shokuhin to Kaihatsu (Food Processing And Ingredients), Vol. 33, No. 2, pp. 42-45 (1998)). Therefore, when applications where edible fat or oil are incorporated in infant formula are taken into consideration, edible fat or oil having low sterol content, that is, having a low unsaponifiable matter content, are strongly desired.

The major part of fat or oil produced by culturing microorganisms belonging to the genus *Mortierella* are accounted for by triglycerides (not less than about 70% by weight) and phospholipids, and unsaponifiable matter is contained as other component. The unsaponifiable matter comprises sterols, such as desmosterol, and sterol esters as main components. Edible fat or oil are in the form of triglycerides. Refined fat or oil, from which phospholipids have been removed, can be provided by subjecting original fat or oil produced by culturing microorganisms (fat or oil which have been provided by extraction of cells and are called "crude oil") to refining processes for edible fat or oil (degumming, deoxidation, deodorization, and decoloration). However, it is difficult to fully remove unsaponifiable matter by the refining processes.

For the reasons that full removal of the unsaponifiable matter is difficult and edible fat or oil having low unsaponifiable matter content are widely desired, studies have been made on how to remove unsaponifiable matter. As a result, refining by column chromatography has been developed (Japanese unexamined Patent Publication (Kokai) No. 10 (1998)-191886). In this technique, however, no detailed studies have been made on components constituting the unsaponifiable matter. A change in components of unsaponifiable matter after refining from the components before the refining, that is, information on which components have been removed by refining, remains unknown.

Fat or oil produced by culturing microorganisms belonging to the genus *Mortierella* are accumulated within mycelia. Therefore, culture should be carried out to give higher cell concentration from the viewpoint of improving the cost effectiveness of the production of highly unsaturated fatty acid-containing fat or oil. In order to provide a high cell concentration, the concentration of nitrogen source of the medium converted to cell components should be increased. According to previous reports (Japanese Unexamined Patent Publications (Kokai) No. 10 (1998)-191886 and No. 10 (1998)-70992), although the unsaponifiable matter or total sterol content is reported, the concentration of the nitrogen source in the medium used in culture of microorganisms is about 1.5% at the highest.

Further, highly unsaturated fatty acid-containing fat or oil having a sterol content of not more than 1% have been reported (Published Japanese Translation of PCT Publication No. 2000-510513). In this case, however, the concentration of a nitrogen source in a medium used in this production is low, and, in the production of a arachidonic acid-containing fat or oil produced using *Mortierella alpina*, culture is carried out in a low nitrogen source concentration of 1% (=yeast extract 0.5%+NaNO$_3$ 0.5%) (Published Japanese Translation of PCT Publication No. 2000-508888). Thus, for the reason that edible fat or oil having low unsaponifiable matter content and sterol content are extensively desired, studies have been made on a reduction in unsaponifiable matter and/or sterols. However, there is no description on unsaponifiable matter and sterols contained in microbial fat or oil produced by high-concentration culture of microorganisms.

As described above, sterols as a main component of unsaponifiable matter are divided into free-type sterols and ester-type sterols. The free-type sterols can be removed by the refining processes, whereas the ester-type sterols can be hardly removed by the refining processes. Therefore, it is considered that, in order to provide refined fat or oil having low unsaponifiable matter content, specifically low sterol contents, the development of a raw material for refining having a low content of ester-type sterols, which cannot be removed by the refining processes without difficulties, that is, a crude oil having low ester type-sterol content, is important.

DISCLOSURE OF THE INVENTION

Thus, the present invention provides a process for producing a crude oil having lowered unsaponifiable matter content and/or ester-type sterol content and comprising a highly unsaturated fatty acid as a constituent fatty acid. Further, the present invention provides a process for producing a refined oil from the crude oil.

Furthermore, the present invention provides a crude oil having lowered unsaponifiable matter content and/or ester-type sterol content and comprising, as a constituent fatty acid, a highly unsaturated fatty acid, which can be produced by the above process, and provides a refined fat or oil produced from this fat or oil.

Furthermore, the present invention provides various uses of the above fat or oil.

Fat or oil having lowered unsaponifiable matter content and sterol content and comprising a highly unsaturated fatty acid as a constituent fatty acid have already been reported (Japanese Unexamined Patent Publication (Kokai) Nos. 10 (1998)-191886 and 10 (1998)-70992, and Published Japanese Translation of PCT Publication No. 2000-510513). These production processes, however, are not suitable for cost-effective production of fat or oil, because the nitrogen source concentration of the medium in the culture is low. Therefore, in order to enhance the cost effectiveness, the amount of highly unsaturated fatty acid-containing fat or oil recovered per culture has been improved by performing culture in an enhanced nitrogen source concentration of the medium. In this case, however, it has been found that the unsaponifiable matter content and the sterol content of the fat or oil are also enhanced. Accordingly, an object of the present invention is to develop a production process which can satisfy both an improvement in cost effectiveness by high-concentration culture and an improvement in quality by a reduction in unsaponifiable matter content and sterol content.

The present inventors have made extensive and intensive studies on culture conditions and chemical compositions of fat or oil produced in media containing a high nitrogen source concentration with a view to providing a fat or oil (crude oil) having lowered unsaponifiable matter content and/or ester-type sterol content and comprising a highly unsaturated fatty acid as a constituent fatty acid produced by high-concentration culture. As a result, surprisingly, an improvement in the form of an agitation impeller of a culture tank and an improvement in pH conditions for sterilization of the medium nitrogen source have led to the establishment of a production process of a fat or oil (crude oil) having an unsaponifiable matter content of not more than 2.2% by weight and/or an ester-type sterol content of not more than 1.0% by weight and comprising a highly unsaturated fatty acid as a constituent fatty acid.

It is known that the supply of a satisfactory amount of oxygen is important for the production of highly unsaturated fatty acids using microorganisms by a liquid culture method (Japanese Unexamined Patent Publication (Kokai) No. 6 (1994)-153970). A volumetric oxygen transfer coefficient (kLa) has been extensively used as an index of oxygen supply in liquid culture of microorganisms. Richard has reported that kLa has a relationship represented by formula (1) with agitation power consumption per unit amount of liquid (Pg/V), aeration linear velocity (Vs), and agitation speed (N) (J. W. Richard; Prog. Ind. Microbiol., vol. 3, p. 141, (1961)).

$$kLa \propto (Pg/V)^{0.4} Vs^{0.5} N^{0.5} \quad (1)$$

Based on measured values of a culture tank having a volume of 0.2 to 60 $m^3$, Fukuda et al. have reported that formula (2) provides better correlation than formula (1) (Fukuda et al., Hakkokogaku Kaishi, vol. 46, p. 829 (1968)).

$$kLa \propto \{(Pg/V)^{0.4} Vs^{0.5} N^{0.5}\}^{1.4} \quad (2)$$

Matsushima et al. have verified the universality of formulae (1) and (2) and have reported that formulae (1) and (2) can be more widely applied by generalization as represented by formula (3) (Matsushima et al., Hakkokogaku Kaishi, vol. 50, p. 105 (1972)).

$$kLa \propto \{(Pg/V)^{0.4} Vs^{0.5} N^{0.5}\}^{\alpha} \quad (3)$$

From these correlation formulae, it is considered that, under identical agitation power consumption (Pg/V) and identical aeration linear velocity (Vs) conditions, a higher agitation speed (N) provides a higher volumetric oxygen transfer coefficient (kLa).

The agitation power requirement per unit amount of liquid is represented by formula (4).

$$Pg/V = \rho Np N^3 d^5 / V \quad (4)$$

wherein $\rho$ represents liquid density, Np represents power number, and d represents diameter of agitation impeller.

In order to provide a higher agitation speed (N) in given work done, that is, identical agitation power requirement, the use of a culture tank having a smaller power number (Np) and a smaller agitation impeller diameter (d) is considered advantageous.

Taguchi et al., (Biseibutsugaku Kisokoza 7-Biseibutu Baiyo Kogaku—(Introduction to Microbiology 7-Microorganism Fermentation Engineering), edited by Hisaharu Taguchi and Shiro Nagai, Kyoritsu Shuppan Co., Ltd. p. 175 (1985)) describes that, regarding standard conditions for an aeration agitation culture tank, d/D ratio is in the range of 1/4 to 1/3 as a standard range and is typically 1/3.

This, however, is established only in water or a culture solution having a low cell concentration. In order to improve the cost effectiveness of the production, the concentration of a nitrogen source in the medium should be increased to give a higher cell concentration. Therefore, the present inventors have thought that, in a culture solution having a high cell concentration, not only the volumetric oxygen transfer coefficient (kLa) but also the mixing of the whole culture solution should be taken into consideration.

Further, it has been found that, when culturing was carried out in a medium having an enhanced nitrogen source concentration, that is, at a higher cell concentration, the unsaponifiable matter content and ester-type sterol content of a fat or oil (crude oil) comprising a highly unsaturated fatty acid as a constituent fatty acid extracted from microorganisms are increased resulting in the production of a fat or oil having an undesired chemical composition due to the culture having an enhanced nitrogen source concentration. Iwamoto has reported that the content of unsaponifiable matter in total lipids decreases with an increase in the fat or oil content of cells ("Biseibutsuniyoru Yushino Seisan (Microbial production of fat or oil)," Hiroaki Iwamoto, (source unknown)). Studies conducted by the present inventors have also shown that the culture in a higher concentration is likely to lower the fat or oil content per cell. The present inventors have considered that the lowered fat or oil content per cell caused an increased unsaponifiable matter content and ester-type sterol content.

Accordingly, the present inventors have considered that, in high-concentration culture in which the concentration of the nitrogen source in the medium is high, what is important is to improve not only the volumetric oxygen transfer coefficient (kLa) but also mixing of the whole culture solution and thus to enhance the fat or oil content per cell. The present inventors have aimed at an improvement in the shape (form) of the agitation impeller as means for achieving this end and have made extensive and intensive studies. As a result, the present inventors have succeeded in enhancing the fat or oil content per cell and in improving the productivity of highly unsaturated fatty acids, by microorganisms in a culture, using a culture tank with d/D (the ratio of the diameter of agitation impeller (=d) to the inner diameter of culture tank (=D)=0.34 to 0.6. Further, it has been surprisingly found that, in this case, the fat or oil comprising a highly unsaturated fatty acid as a constituent fatty acid extracted from the microorganism had a significantly lowered ester-type sterol content.

Further, it has been found that, even in the case of a culture tank with d/D=less than 0.34, an improvement in productivity of a highly unsaturated fatty acid by microorganisms and a reduction in ester-type sterol content can be achieved by sterilizing the nitrogen source in the medium at a pH value of not more than 5.0.

Based on this, the present inventors have made extensive and intensive studies and, as a result, have succeeded in stably producing a fat or oil (crude oil) having lowered unsaponifiable matter content and/or ester-type sterol content by adopting a method wherein culture is carried out using a culture tank provided with an agitation impeller with d/D=not less than 0.34, or by adopting a method wherein, in the case of a culture tank with d/D=less than 0.34, culture is carried out in a medium containing a nitrogen source which has been sterilized at a pH value of not more then 5. This has led to the completion of the present invention.

Accordingly, the present invention provides a process for producing a crude oil having lowered unsaponifiable matter content and/or ester-type sterol content and comprising a highly unsaturated fatty acid as a constituent fatty acid, characterized in that a microorganism capable of producing a fat or oil comprising an unsaturated fatty acid as a constituent fatty acid is cultured in a medium containing a nitrogen source concentration of 2 to 15% within a culture tank equipped with an agitation impeller satisfying the requirement that the ratio of the diameter of agitation impeller (=d) to the inner diameter of the culture tank (=D) is d/D=0.30 to 0.6.

The present invention also provides a crude oil characterized by having an unsaponifiable matter content of not more than 2.2% by weight produced by the above process. The present invention also provides a refined fat or oil produced by refining the above crude oil.

The present invention also provides a general food and drink, a functional food, a nutrition supplement, an infant formula for premature babies, an infant formula for mature babies, a food for infants, a food for expectant and nursing mothers, or a food for aged persons, comprising the above crude oil and/or the above refined fat or oil incorporated therein.

The present invention also provides a therapeutic nutrition food comprising the above crude oil and/or the above refined fat or oil incorporated therein optionally together with a neutral carrier suitable for oral, intrarectal or parenteral administration.

The present invention also provides a food for animals or fishes, comprising the above crude oil and/or the above refined fat or oil incorporated therein.

The present invention also provides a pharmaceutical composition, comprising the above crude oil and/or the above refined fat or oil incorporated therein. The present invention also provides a pharmaceutical composition prepared by using the above crude oil and/or the above refined fat or oil as a raw material.

EMBODIMENTS OF THE INVENTION

The present invention relates to a process for producing a fat or oil (crude oil) having lowered unsaponifiable matter and/or ester-type sterol content and comprising a highly unsaturated fatty acid as a constituent fatty acid, said fat or oil (crude oil), and foods and drinks, therapeutic nutritional foods, animal foods, and pharmaceutical preparations, with a refined fat or oil (triglyceride) provided by refining the fat or oil (crude oil) incorporated therein.

The fat or oil (crude oil) according to the present invention is a microbial fat or oil obtained from a culture product prepared by culturing a microorganism capable of producing a fat or oil comprising a highly unsaturated fatty acid as a constituent fatty acid in a medium containing a nitrogen source concentration of 2 to 15%. The fat or oil (crude oil) has lowered unsaponifiable matter and/or ester-type sterol content achieved by culture in a culture tank provided with an agitation impeller of d/D=0.34 to 0.6, or by culture in a nitrogen source-containing medium sterilized at a pH value of not more than 5 when a culture tank of d/D=less than 0.34 is used.

Specifically, the fat or oil (crude oil) has an unsaponifiable matter content of not more than 2.2% by weight, preferably not more than 2.0% by weight, more preferably not more than 1.8% by weight and/or an ester-type sterol content of not more than 1.0% by weight, preferably not more than 0.8% by weight, more preferably not more than 0.6% by weight, and a highly unsaturated fatty acid content, based on total fatty acid in the fat or oil (crude oil), of not less than 10% by weight, preferably not less than 20% by weight, more preferably not less than 30% by weight, most preferably not less than 40% by weight. Therefore, culture of a microorganism capable of producing a fat or oil (triglyceride) comprising a highly unsaturated fatty acid as a constituent fatty acid should be carried out.

Microorganisms referred to herein are desirably microorganisms which can produce, mainly as a constituent fatty acid of triglyceride, at least one highly unsaturated fatty acid selected from ω6 highly unsaturated fatty acids having 18 or more carbon atoms and 3 or more double bonds, ω9 highly unsaturated fatty acids having 18 or more carbon atoms and 2 or more double bonds, and ω3 highly unsaturated fatty acids having 18 or more carbon atoms and 3 or more double bonds.

ω6 highly unsaturated fatty acids having 18 or more carbon atoms and 3 or more double bonds include γ-linolenic acid (6,9,12-octadecatrienoic acid), dihomo-γ-linolenic acid (8,11,14-eicosatrienoic acid), arachidonic acid (5,8,11,14-eicosatetraenoic acid), 7,10,13,16-docosatetraenoic acid (22:4 ω6), and DPA ω6 (4,7,10,13,16-docosapentaenoic acid). ω9 highly unsaturated fatty acids having 18 or more carbon atoms and 2 or more double bonds include 6,9-octadecadienoic acid, 8,11-eicosadienoic acid, and Mead acid (5,8,11-eicosatrienoic acid), and ω3 highly unsaturated fatty acids having 18 or more carbon atoms and 3 or more double bonds include α-linolenic acid (9,12,15-octadecatrienoic acid), 6,9,12,15-octadecatetraenoic acid (18:4 ω3), 8,11,14,17-eicosatetraenoic acid (20:4 ω3), EPA (5,8,11,14,17-eicosapentaenoic acid), DPAω3 (7,10,13,16,19-docosapentaenoic acid), and DHA (4,7,10,13,16,19-docosahexaenoic acid.

Accordingly, in the present invention, all microorganisms can be used so long as they can produce fat or oil (triglycerides) comprising highly unsaturated fatty acids as constituent fatty acids. Microorganisms capable of producing fat or oil (triglycerides) comprising arachidonic acid as constituent fatty acids include, for example, microorganisms belonging to the genus *Mortierella, Conidiobolus, Pythium, Phytophthora, Penicillium, Cladosporium, Mucor, Fusarium, Aspergillus, Rhodotorula, Entomophthora, Echinosporangium,* and *Saprolegnia.*

Microorganisms belonging to the subgenus *Mortierella* of the genus *Mortierella* include, for example, subgenus *Mortierella elongata, Mortierella exigua, Mortierella hygrophila,* and *Mortierella alpina.* Specific examples thereof include *Mortierella elongata* (IFO 8570), *Mortierella exigua* (IFO 8571), *Mortierella hygrophila* (IFO 5941), *Mortierella alpina* (IFO 8568), ATCC 16266, ATCC 32221, ATCC 42430, CBS 219.35, CBS 224.37, CBS 250.53, CBS 343.66, CBS 527.72, CBS 529.72, CBS 608.70, and CBS 754.68 strains.

For example, microorganisms belonging to the genus *Crypthecodenium, Thrautochytrium, Schizochytrium, Ulkenia, Japonochytrium,* or *Haliphthoros* may also be mentioned as microorganisms capable of producing DHA.

All of these strains are available without any restriction from the Institute for Fermentation, Osaka (IFO), American Type Culture Collection (ATCC), and Centrralbureau voor Schimmelcultures (CBS). Further, a strain isolated from soil by a research group involved in the present invention, i.e., *Mortierella elongata* SAM 0219 (FERM P-8703) (FERM BP-1239) may also be used.

In order to culture the strain used in the present invention, spores, mycelia, or a seed culture solution obtained by culturing in advance or cells collected from the seed culture are inoculated into a liquid medium, followed by main culture. In the case of a liquid medium, carbon sources usable herein include, but are not limited to, those commonly used in the art, for example, glucose, fructose, xylose, saccharose, maltose, soluble starch, molasses, glycerol, mannitol and saccharified starches.

Nitrogen sources include natural nitrogen sources such as peptones, yeast extracts, malt extracts, meat extracts, casamino acids, corn steep liquors, soybean proteins, defatted soybeans, and cotton seed meals, organic nitrogen sources such as urea, and inorganic nitrogen sources such as sodium nitrate, ammonium nitrate, and ammonium sulfate. In particular, nitrogen sources obtained from soybeans, specifically soybeans, defatted soybeans, soybean flakes, edible soybean proteins, bean-curd refuse, soymilk, and soybean flour, may be mentioned as the nitrogen source. In particular, heat-denatured defatted soybeans, more preferably products prepared by heat treating defatted soybeans at about 70 to 90° C. and removing an ethanol-soluble component may be used solely or in a combination of two or more of them or in a combination thereof with the above nitrogen source.

Further, if necessary, phosphate ions, potassium ions, sodium ions, magnesium ions, calcium ions, and, in addition, metal ions such as iron, copper, zinc, manganese, nickel, and cobalt ions, and vitamin may also be used as minor nutrients.

The concentrations of these medium components are not particularly limited so far as the growth of microorganisms is not inhibited. In practice, the total amount of the carbon sources added is generally 0.1 to 40% by weight, preferably 1 to 25% by weight, and the total amount of the nitrogen sources added is preferably 2 to 15% by weight, more preferably 2 to 10% by weight. More preferably, the initial amount of the carbon sources added is 1 to 5% by weight, and the initial amount of the nitrogen sources added is 3 to 8% by weight, and, in the course of culture, the carbon source and the nitrogen source and, more preferably, only the carbon source may be fed.

In order to increase the yield of unsaturated fatty acids, for example, hydrocarbons such as hexadecane or octadecane; fatty acids or salts thereof such as oleic acid or linoleic acid, or fatty acid esters, for example, ethyl esters, glycerin fatty acid esters, or sorbitan fatty acid esters; or fat or oil such as olive oils, soybean oils, rapeseed oils, cotton seed oils or palm oils may be used, as precursors of unsaturated fatty acids, either solely or in combination. The amount of the substrate added is 0.001 to 10%, preferably 0.5 to 10%, based on the medium. Culture may also be carried out using these substrates as a sole carbon source.

The culture temperature of microorganisms, which produce highly unsaturated fatty acids, varies depending upon the microorganism used. However, the culture temperature may be 5 to 40° C., preferably 20 to 30° C. A method may also be used wherein culture is carried out at 20 to 30° C. to grow cells and the culture is then continued at 5 to 20° C. to produce unsaturated fatty acids. The proportion of a highly unsaturated fatty acid in the produced fatty acid can also be increased by this temperature control. Seed culture is carried out by aeration-agitation culture, shaking culture, solid culture, or stationary liquid culture, and main culture is carried out by aeration-agitation culture. The medium at the time of the start of the main culture (at the time of the inoculation of seed culture solution) is adjusted to pH 5 to 7, preferably 5.5 to 6.5. The main culture is generally carried out for 2 to 30 days, preferably 5 to 20 days, more preferably 5 to 15 days.

The fat or oil (crude oil) according to the present invention is a microbial fat or oil obtained from a culture product prepared by culturing a microorganism capable of producing a fat or oil (triglyceride) comprising a highly unsaturated fatty acid as a constituent fatty acid, and the most characteristic feature of the present invention is that the unsaponifiable matter content and/or ester-type sterol content of the crude oil are reduced by main culture in a culture tank provided with an agitation impeller of d/D=0.34 to 0.6, or by main culture in a nitrogen source-containing medium sterilized at a pH value of not more than 5 when a culture tank of d/D=less than 0.34 is used. Thus, the present invention has developed a method which can lower the content of unsaponifiable matter content and/or ester-type sterol content in the crude oil by using microorganisms capable of producing fat or oil (triglycerides) comprising highly unsaturated fatty acids as a constituent fatty acid.

In the culture method according to the present invention, the most characteristic feature is that the unsaponifiable matter content and/or ester-type sterol content in the crude oil are lowered by culture in a culture tank of d/D (the ratio of the diameter of agitation impeller (=d) to the inner diameter of culture tank (=D))=0.30 to 0.6, preferably d/D=0.34 to 0.55, more preferably d/D=0.37 to 0.55, most preferably d/D=0.42 to 0.55. In order to attain better effect by the d/D ratio, the use of a culture tank having a volume of not less than 1 $m^3$, preferably not less than 5 $m^3$, more preferably not less than 10 $m^3$, is desired. Regarding the agitation impeller, agitation impellers including turbine blades may be used in one stage or in a plurality of stages without particular limitation.

When pH adjustment of the medium is carried out after the sterilization of the medium, the adjustment procedure should be carried out aseptically with caution so as not to cause contamination with unwanted microorganism. Therefore, the pH adjustment is generally carried out before the sterilization of the medium. For example, when a medium, which does not cause any pH change upon sterilization, is adjusted to pH 6.0 at the time of the start of culture, pH adjustment of the medium in an nonaseptic manner to 6.0 before sterilization eliminates the need to aseptic pH adjustment after the sterilization. In order to reduce the ester-type sterol even in a culture tank of d/D=less than 0.34, the present inventors have aimed at and have made studies on the influence of pH condition in the step of sterilization on the productivity of culture and the composition of the product. As a result, the present inventors have found that, before sterilization of a medium adjusted to pH not more than 5, readjustment of pH to a value suitable for the start of culture after the sterilization is preferred.

Specifically, a solution containing a medium nitrogen source is adjusted to pH 4 to 5, preferably pH 4.2 to 4.7, followed by sterilization. The sterilized medium as such or optionally after addition of another medium to be sterilized is used to prepare a culture initiation medium which is then adjusted to pH 5 to 7, preferably pH 5.5 to 6.5. A seed culture solution is inoculated into the medium to start main culture. pH adjustors usable for adjusting pH of the nitrogen source-containing solution before the sterilization include, but are not particularly limited to, sulfuric acid, hydrochloric acid, phosphoric acid, nitric acid, and carbonic acid or salts thereof which are used solely or in a combination of two or more of them. Readjustors for pH of the medium after the sterilization include, but are not particularly limited to, hydroxide compounds such as sodium hydroxide and potassium hydroxide and ammonia and ammonium salts which used solely or in a combination of two or more of them.

Microorganisms belonging to the subgenus *Mortierella* of the genus *Mortierella* are known to be able to produce fat or oil (triglycerides) comprising arachidonic acid as a main constituent fatty acid. The present inventors have obtained microorganisms capable of producing fat or oil (triglyceride) comprising dihomo-γ-linolenic acid as a main constituent fatty acid (Japanese Unexamined Patent Publication (Kokai) No. 5 (1993)-91887) and microorganisms capable of producing fat or oil comprising ω9 highly unsaturated fatty acids as a main constituent fatty acid (triglyceride) (Japanese Unexamined Patent Publication (Kokai) No. 5 (1993)-91888) by subjecting the above strains to mutation treatment.

Further, the present inventors have also obtained microorganisms resistant to a highly concentrated carbon source (WO 98/39468). The above microorganisms are microorganisms belonging to the subgenus *Mortierella* of the genus *Mortierella*, and the unsaponifiable matter content and/or ester-type sterol content of a crude oil can be easily lowered by the culture method of the present invention, specifically by main culture in a culture tank provided with an agitation impeller of d/D=0.34 to 0.6, or by main culture in a nitrogen source-containing medium sterilized at a pH value of not more than 5 and having a medium nitrogen source concentration of 2 to 15% when a culture tank of d/D=less than 0.34 is used.

The microorganisms used in the present invention, however, are not limited to those belonging to the subgenus *Mortierella* of the genus *Mortierella*, and contemplated crude oils having lowered unsaponifiable matter content and/or ester-type sterol content can be produced by applying, to microorganisms capable of producing fat or oil (triglycerides) comprising a highly unsaturated fatty acid as a constituent fatty acid, the culture method according to the present invention, specifically by main culture in a culture tank provided with an agitation impeller of d/D=0.34 to 0.6, or by main culture in a nitrogen source-containing medium sterilized at a pH value of not more than 5 and having a medium nitrogen source concentration of 2 to 15% when a culture tank of d/D=less than 0.34 is used.

Methods usable for obtaining a crude oil from microorganisms, which have accumulated a fat or oil comprising a highly unsaturated fatty acid as a constituent fatty acid having lowered unsaponifiable matter content and/or ester-type sterol content produced by main culture in a culture tank provided with an agitation impeller of d/D=0.34 to 0.6, or by main culture in a nitrogen source-containing medium sterilized at a pH value of not more than 5 and having a medium nitrogen source concentration of 2 to 15% when a culture tank of d/D=less than 0.34 is used, include a method in which, after the completion of the culture, the culture solution as such or after treatment such as sterilization, concentration, or acidification is subjected to conventional solid-liquid separation means, such as plain sedimentation, centrifugation and/or filtration, to collect cultured cells.

Coagulating agents or filtration aids may be added from the viewpoint of aiding solid-liquid separation. Coagulating agents include, for example, aluminum chloride, calcium chloride, algin, and chitosan. Filtration aids include, for example, diatomaceous earth. Cultured cells are preferably washed with water, crushed, and dried. Drying may be carried out, e.g., by lyophilization, air drying, or fluidized bed drying. Means for obtaining a crude oil from dried cells may be extraction with an organic solvent or squeezing. Extraction with an organic solvent under a nitrogen gas stream, however, is preferred.

Organic solvents include ethanol, hexane, methanol, ethanol, chloroform, dichloromethane, petroleum ether, and acetone. Alternating extraction with methanol and petroleum ether and extraction with a single-phase solvent of chloroform-methanol-water may also be used. Extraction methods for obtaining the crude oil, however, are not limited to the above methods, and any method, which can be efficiently extract fat or oil accumulated within the cells, may be used. For example, supercritical extraction may be used as an effective method.

A target crude oil can be obtained by removing the organic solvent or supercritical fluid component from the extract obtained by extraction with the organic solvent or the supercritical fluid under reduced pressure or other conditions. Further, alternatively, extraction may be carried out using wet cells. In this case, solvents compatible with water, such as methanol, ethanol, and acetone, or mixed solvents compatible with water and composed of the above solvents and water and/or other solvents are used. The other procedures are the same as those described above.

The crude oil having lowered unsaponifiable matter content and/or ester-type sterol content and comprising a highly unsaturated fatty acid as a constituent fatty acid produced according to the present invention may be blended with an animal food for direct use. When application to foods is taken into consideration, however, before use, the crude oil is preferably subjected to a conventional fat or oil refining process. Fat or oil refining processes usable herein include conventional processes such as degumming, deoxidation, deodorization, decoloration, column treatment, molecular distillation, and wintering. Therefore, refined fat or oil, of which the unsaponifiable matter content and/or ester-type sterol content have been unprecedentedly lowered, can be obtained by subjecting the crude oil according to the present invention, having lowered ester-type sterol content unattainable by the conventional fat or oil refining process, to fat or oil refining processes.

The process load in the refining process can also be lowered by subjecting the crude oil, according to the present invention and having lowered ester-type sterol content, to the fat or oil refining process. Specifically, for example, a refined fat or oil having unsaponifiable matter content and/or ester-type sterol content equal to that in the prior art can be provided even after a reduction in treatment time of the refining process and a reduction in energy cost. Further, a refined fat or oil having unsaponifiable matter content and/or ester-type sterol content, which are lower than that in the prior art technique, can be provided using the same treatment time and energy cost as the prior art technique.

The refined fat or oil (triglyceride) according to the present invention is usable in an infinite range of applications, for example, in raw materials and additives for foods, beverages, cosmetics, and pharmaceutical preparations, and the purpose and amount of use are not limited.

For example, food compositions, in which the refined fat or oil can be used, include general foods and, in addition, functional foods, nutrition supplements, formula for premature babies, formula for mature babies, formula for infants, foods for infants, foods for expectant and nursing mothers, or foods for aged persons.

Examples of foods containing fat or oil include: natural foods inherently containing fat or oil, such as meat, fish, or nuts; foods to which fat or oil are added at the time of cooking, such as soups; foods using fat or oil as a heating medium, such as doughnuts; fat or oil foods such as butter; processed foods to which fat or oil are added at the time of processing, such as cookies or biscuits; or foods on which fat or oil are sprayed or coated at the time of finish processing, such as hard biscuits. Further, the refined fat or oil can be added to fat-and-oil-free agricultural foods, fermented foods, livestock foods, marine foods, or beverages. The refined fat or oil may be used in the form of functional foods and pharmaceutical preparations, for example, may be used in processed forms such as enteral nutrients, powders, granules, troches, liquids for internal use, suspensions, emulsions, and syrups.

EXAMPLES

The present invention will be described in more detail with reference to the following examples. However, it should be noted that the present invention is not limited to these examples only.

Example 1

Production of Arachidonic Acid, d/D=0.34, Concentration of Soy Flour in Medium=6%

*Mortierella alpina* (CBS 754.68) was provided as an arachidonic acid-producing fungus. A standard strain of *Mortierella alpina* was inoculated into a medium (1% yeast extract, 2% glucose, pH 6.3). Seed culture (first stage) was started under conditions of reciprocating shaking at 100 rpm and temperature 28° C., and the seed culture was continued for 3 days. Next, 30 L of a medium (1% yeast extract, 2% glucose, 0.1% soybean oil, pH 6.3) was prepared in a 50 L-volume aeration-agitation culture tank. The seed culture (first stage) solution was inoculated into the medium. Seed culture (second stage) was started under conditions of agitation speed 200 rpm, temperature 28° C., and inner pressure of tank 150 kPa, and the seed culture was continued for 2 days.

Next, 4500 L of a medium (medium A: soy flour 336 kg, $KH_2PO_4$ 16.8 kg, $MgCl_2 \cdot 6H_2O$ 2.8 kg, $CaCl_2 \cdot 2H_2O$ 2.8 kg, soybean oil 5.6 kg) was prepared. The medium was adjusted to pH 6.3 for condition (1-1) and to pH 4.5 for condition (1-2). Both the medium for condition (1-1) and the medium for condition (1-2) were sterilized under conditions of 121° C. and 20 min. Medium C was prepared as another medium by sterilizing 1000 L of a medium (medium B: glucose monohydrate 112 kg) under conditions of 140° C. for 40 sec and adding the sterilized medium to the above medium A. Medium C as such was used for condition (1-1), and medium C was adjusted to pH 6.3 for condition (1-2). The seed culture (second stage) solution was then inoculated into the media thus prepared, and the volume was adjusted to an initial amount of culture solution of 5600 L in total (volume of culture tank: 10 kL).

Culture was started under conditions of temperature 26° C., air flow rate 49 $Nm^3/hr$, and inner pressure 200 kPa.

The form of the culture tank was such that six-blade turbines were provided in three stages and the ratio of the diameter of the agitation impeller (=d) to the inner diameter of the tank (=D) was d/D=0.34. While feeding a medium as shown in Table 1, main culture was carried out for 306 hr. At the end of the culture, the amount of the culture solution was 7750 L due to the influence of an increase in amount of the solution by the feeding of the medium and a decrease in amount of the solution by evaporation of the solution. At the end of the culture, the concentration of arachidonic acid produced per liter of the culture solution was 18.2 g/L for condition (1-1) and 18.4 g/L for condition (1-2).

TABLE 1

| Medium feeding in Example 1 | |
|---|---|
| Main culture time | Medium fed |
| After 19 hours | glucose monohydrate 280 kg/460 L |
| After 43 hours | glucose monohydrate 280 kg/450 L |
| After 67 hours | glucose monohydrate 252 kg/390 L |
| After 91 hours | glucose monohydrate 252 kg/410 L |
| After 120 hours | glucose monohydrate 224 kg/370 L |
| After 140 hours | glucose monohydrate 168 kg/280 L |
| After 163 hours | glucose monohydrate 168 kg/270 L |

After the completion of the culture, the culture solution was sterilized under conditions of 120° C. for 20 min. Wet cells were then collected by a continuous dehydrator. The collected wet cells were dried in a vibration fluidized bed dryer to a water content of 1% by weight. The dried cells were transported by an air transport machine to a filling place and, together with nitrogen gas, were filled into a container bag of an aluminum pouch having a volume of about 1 $m^3$. The mouth part of the bag was heat sealed, and the container bag was then stored in a refrigerator of 10° C. or below.

The dried cells were taken out of the container bag and were subjected to extraction with hexane. The solid matter was removed from the hexane solution by filtration. The filtrate was then heated under reduced pressure to remove hexane to give a crude oil comprising arachidonic acid as a constituent fatty acid. The crude oil was analyzed. As a result, as shown in Table 2, the crude oil had a low ester-type sterol content.

TABLE 2

| Found for arachidonic acid-containing crude oil | | |
|---|---|---|
| | Example | |
| | Example 1 Condition 1-1 | Example 1 Condition 1-2 |
| Form of culture tank, d/D | 0.34 | 0.34 |
| Adjusted pH value of medium A (before sterilization) | 6.3 | 4.5 |
| pH value of medium C (after sterilization and before inoculation of seed culture solution) | 6.3 | 6.3 |
| Wt % of each fraction | | |
| Triglyceride | 94.0% | 94.2% |
| Unsaponifiable matter | 2.0% | 1.8% |
| Ester-type sterol | 0.8% | 0.6% |
| Arachidonic acid in total fatty acid in crude oil, % | 42.0% | 42.1% |

Example 2

Production of Arachidonic Acid, d/D=0.42, Concentration of Soy Flour in Medium=6%

Seed culture was carried out in the same manner as in Example 1. Main culture was carried out under the same conditions as in condition (1-1) in Example 1, except that the form of the culture tank was such that six-blade turbines of d/D=0.42 were provided in three stages and pH conditions for the preparation of the medium were varied. For culture under condition (2-1), medium A (before sterilization) was adjusted to pH 6.1, and no pH adjustment was carried out for medium C (before inoculation of seed culture solution). For culture under condition (2-2), medium A was adjusted to pH 4.5, and medium C was adjusted to pH 6.1. As a result of the culture, the concentration of arachidonic acid produced per liter of culture solution at the end of the culture was 19.0 g/L for condition (2-1) and 19.7 g/L for condition (2-2). After the completion of the culture, a crude oil comprising arachidonic acid as a constituent fatty acid was obtained in the same manner as in Example 1. The crude oil was analyzed. As a result, as shown in Table 3, the crude oil had a low ester-type sterol content.

TABLE 3

Found for arachidonic acid-containing crude oil

| | Example | |
|---|---|---|
| | Example 2 Condition 2-1 | Example 2 Condition 2-2 |
| Form of culture tank, d/D | 0.42 | 0.42 |
| Adjusted pH value of medium A (before sterilization) | 6.1 | 4.5 |
| pH value of medium C (after sterilization and before inoculation of seed culture solution) Wt % of each fraction | 6.1 | 6.1 |
| Triglyceride | 94.2% | 93.5% |
| Unsaponifiable matter | 1.8% | 1.6% |
| Ester-type sterol | 0.6% | 0.5% |
| Arachidonic acid in total fatty acid in crude oil, % | 42.2% | 41.3% |

Example 3

Production of Arachidonic Acid, d/D=0.3, 0.25, and 0.2, Concentration of Soy Flour in Medium=6%

Seed culture was carried out in the same manner as in Example 1. Main culture was carried out under the same conditions as in condition (1-1) in Example 1, except that, regarding the form of the culture tank, a tank provided with six-blade turbines of d/D=0.3 in two stages, a tank provided with six-blade turbines of d/D=0.25 in two stages, and a tank provided with six-blade turbines of d/D=0.2 in two stages were used. As a result of the culture, the concentration of arachidonic acid produced per liter of culture solution at the end of the culture was 17.0 g/L for the tank of d/D=0.30, 16.5 g/L for the tank of d/D=0.25, and 13.5 g/L for the tank of d/D=0.2. After the completion of the culture, a crude oil comprising arachidonic acid as a constituent fatty acid was obtained in the same manner as in Example 1. The crude oil was analyzed. As a result, as shown in Table 4, for all the cases, the ester-type sterol content exceeded 1%. From comparison of the results of Example 3 with the results of Examples 1 and 2, the high ester-type sterol content is considered attributable to the culture tank with a low d/D ratio.

TABLE 4

Found values for arachidonic acid-containing crude oil

| | Example or control example | | |
|---|---|---|---|
| | Example 3 Control example | Example 3 Control example | Example 3 Control example |
| Form of culture tank, d/D | 0.30 | 0.25 | 0.20 |
| Adjusted pH value of medium A (before sterilization) | 6.3 | 6.3 | 6.3 |
| pH value of medium C (after sterilization and before inoculation of seed culture solution) Wt % of each fraction | 6.3 | 6.3 | 6.3 |
| Triglyceride | 93.8% | 93.1% | 93.0% |
| Unsaponifiable matter | 2.9% | 2.9% | 2.9% |
| Ester-type sterol | 1.2% | 1.2% | 1.2% |
| Arachidonic acid in total fatty acid in crude oil, % | 42.0% | 41.6% | 41.5% |

Example 4

Production of Arachidonic Acid, d/D=0.3, 0.25, and 0.2, Concentration of Soy Flour in Medium=6%, Low pH Sterilization Seed culture was carried out in the same manner as in Example 1. PH adjustment of the medium in the main culture was carried out in the same manner as in condition (1-2) in Example 1 (medium A (pH 4.5) sterilization→medium C (pH 6.3)). Thereafter, the main culture was carried out under three conditions in total, i.e., condition 4-1 in which a tank provided with six-blade turbines of d/D=0.3 in two stages, condition 4-2 in which a tank provided with six-blade turbines of d/D=0.25 in two stages, and condition 4-3 in which a tank provided with six-blade turbines of d/D=0.2 in two stages in the same manner as in Example 1. In addition to the above experiments, culture was carried out using a tank of d/D=0.3 under such additional two conditions that medium A was adjusted to pH 4.0 for condition 4-4 and pH 4.9 for condition 4-5.

As a result of the main culture, the concentration of arachidonic acid produced per liter of culture solution at the end of the culture was 17.2 g/L for condition (4-1) [sterilization at pH 4.5, d/D=0.30], 16.8 g/L for condition (4-2) [sterilization at pH 4.5, d/D=0.25], 14.0 g/L for condition (4-3) [sterilization at pH 4.5, d/D=0.20], 17.1 g/L for condition (4-4) [sterilization at pH 4.0, d/D=0.30], and 17.2 g/L for condition (4-5) [sterilization at pH 4.9, d/D=0.30]. After the completion of the culture, the procedure of Example 1 was repeated to give a crude oil comprising arachidonic acid as a constituent fatty acid.

The results of analysis of the crude oil are shown in Table 5. Comparison of the results of Example 3 with the results of Example 4 shows that, in the culture tank of d/D=0.30, sterilization of the nitrogen source of the medium at pH 4.5 could reduce the ester-type sterol content to not more than 1%. In the culture tank of d/D=0.25 and the tank of d/D=0.20, however, despite sterilization of the nitrogen source at pH 4.5, the ester-type sterol content could not be reduced to not more than 1%. Further, comparison among the results of conditions (4-1), (4-4), and (4-5) shows that sterilization of the nigrogen source at pH in the range of 4.0 to 4.9 is considered to provide equal ester-type sterol reduction results.

TABLE 5

Found values for arachidonic acid-containing crude oil

| | Example or control example | | | | |
|---|---|---|---|---|---|
| | Example 4 Condition 4-1 | Example 4 Condition 4-2 (control example) | Example 4 Condition 4-3 (control example) | Example 4 Condition 4-4 | Example 4 Condition 4-5 |
| Form of culture tank, d/D | 0.30 | 0.25 | 0.20 | 0.30 | 0.30 |
| Adjusted pH value of medium A (before sterilization) | 4.5 | 4.5 | 4.5 | 4.0 | 4.9 |
| pH value of medium C (after sterilization and before inoculation of seed culture solution) | 6.3 | 6.3 | 6.3 | 6.3 | 6.3 |
| Wt % of each fraction | | | | | |
| Triglyceride | 93.8% | 93.1% | 93.0% | 93.5% | 93.4% |
| Unsaponifiable matter | 2.2% | 2.5% | 2.7% | 2.1% | 2.1% |
| Ester-type sterol | 1.0% | 1.1% | 1.1% | 1.0% | 1.0% |
| Arachidonic acid in total fatty acid in crude oil, % | 42.0% | 40.8% | 40.8% | 41.5% | 41.7% |

Example 5

Results of Analysis of Refined Fat or Oil Provided by Refining Crude Oil

Arachidonic acid-containing crude oils prepared in condition (1-1) in Example 1 and condition (2-1) in Example 2 were refined by conventional deoxidation and degumming methods to give refined fat or oil 5-A and 5-B. The arachidonic acid-containing crude oil prepared in condition d/D=0.25 in Example 3 was refined in the same manner as described just above to give refined fat or oil 5-C. The found values for the arachidonic acid-containing refined fat or oil are shown in Table 6.

TABLE 6

Results of analysis of Example 5 (found values for arachidonic acid-containing refined fat or oil A, B, and C)

| | Example or control example | | |
|---|---|---|---|
| | Example 1 (Condition 1-1) | Example 2 (Condition 2-1) | Example 3 (d/D = 0.25) (Control example) |
| Refined fat or oil | 5-A | 5-B | 5-C |
| Wt % of each fraction | | | |
| Triglyceride | 96.0% | 96.4% | 95.0% |
| Unsaponifiable matter | 1.4% | 1.2% | 2.0% |
| Ester-type sterol | 0.8% | 0.6% | 1.2% |
| Arachidonic acid in total fatty acid in refined fat and oil, % | 42.4% | 42.8% | 41.7% |

Example 6

Production of Arachidonic Acid Under Condition of 1.5% of Soy Flour

*Mortierella alpina* (CBS 754.68) was provided, and seed culture (first stage and second stage) was carried out in the same manner as in Example 1. Next, 4500 L of a medium (medium A: soy flour 84 kg, $KH_2PO_4$ 16.8 kg, $MgCl_2.6H_2O$ 2.8 kg, $CaCl_2.2H_2O$ 2.8 kg, soybean oil 5.6 kg) was sterilized under conditions of 121° C. and 20 min. Medium C was prepared as another medium by sterilizing 1000 L of a medium (medium B: glucose monohydrate 112 kg) under conditions of 140° C. for 40 sec and adding the sterilized medium to the above medium A.

Medium C was adjusted to pH 6.1. The seed culture (second stage) solution was then inoculated into the media thus prepared, and the volume was adjusted to an initial amount of culture solution of 5600 L in total (volume of culture tank: 10 kL). Main culture was started under conditions of temperature 26° C., air flow rate 49 $Nm^3$/hr, and inner pressure 200 kPa. The main culture was carried out in main culture tanks, i.e., a culture tank provided with six-blade turbines of d/D (ratio of diameter of agitation impeller (=d) to inner diameter of tank (=D))=0.34 in two stages and a culture tank provided with six-blade turbines of d/D=0.25 in two stages. While feeding a medium as shown in Table 7, main culture was carried out for 162 hr. At the end of the culture, the concentration of arachidonic acid produced per liter of the culture solution was 5.0 g/L for the tank of d/D=0.34 and 4.7 g/L for the tank of d/D=0.25.

TABLE 7

Medium feeding in Example 6

| Main culture time | Medium fed |
|---|---|
| After 19 hours | glucose monohydrate 84 kg/200 L |
| After 43 hours | glucose monohydrate 84 kg/200 L |
| After 67 hours | glucose monohydrate 56 kg/120 L |
| After 91 hours | glucose monohydrate 56 kg/125 L |

After the completion of the culture, in the same manner as in Example 1, dried cells were collected, followed by extraction with hexane to give a crude oil comprising arachidonic acid as a constituent fatty acid. Found values for the crude oil are shown in Table 8. When the concentration of a nitrogen source in the medium was 1.5%, for both d/D=0.25 and d/D=0.34, the crude oil had an ester-type sterol content of not more than 1%.

TABLE 8

Results of Example 6 (found values for arachidonic acid-containing crude oil)

| Form of culture tank, d/D Wt % of each fraction | 0.25 | 0.34 |
|---|---|---|
| Triglyceride | 94.1% | 93.0% |
| Unsaponifiable matter | 1.2% | 1.2% |
| Ester-type sterol | 0.4% | 0.4% |
| Arachidonic acid in total fatty acid in crude oil, % | 40.8% | 41.5% |

Example 7

Production of Dihomo-γ-Linolenic Acid; Influence of d/D=0.30, 0.34, and 0.25, Concentration of Soy Flour in Medium 4%, and Nitrogen Source Sterilization pH 4.5

The present inventors have established a production process of a fat or oil (triglyceride) comprising dihomo-γ-linoleinic acid as a constituent fatty acid. The fat or oil can be produced by culturing microorganisms having arachidonic acid producing capability and lowered Δ5 unsaturation activity, for example, a mutant *Moltierella alpina* SAM 1860 strain (FERM P-3589) according to the production process described in Japanese Unexamined Patent Publication (Kokai) No. 5 (1993)-91887.

*Mortierella alpina* (SAM 1860) was provided as a dihomo-γ-linolenic acid-producing fungus. A standard strain of *Mortierella alpina* was inoculated into a medium (1% yeast extract, 2% glucose, pH 6.3) in an amount of 100 mL contained in a 500 mL Erlenmeyer flask. Seed culture (first stage) was started under conditions of reciprocating shaking 100 rpm and temperature 28° C., and the seed culture was continued for 3 days. Next, 30 L of a medium (1% yeast extract, 2% glucose, 0.1% soybean oil, pH 6.3) was prepared in a 50 L-volume aeration-agitation culture tank. The seed culture (first stage) solution was inoculated into the medium. Seed culture (second stage) was started under conditions of agitation speed 200 rpm, temperature 28° C., and inner pressure of tank 150 kPa, and the seed culture was continued for 2 days. The main culture was carried out on four levels of conditions (7-1) to (7-4).

For condition (7-1), 4500 L of a medium (medium A: soy flour 224 kg, $KH_2PO_4$ 16.8 kg, $MgCl_2.6H_2O$ 2.8 kg, $CaCl_2.2H_2O$ 2.8 kg, soybean oil 5.6 kg) was adjusted to pH 6.1 by the addition of an aqueous sodium hydroxide solution, and the medium was then sterilized under conditions of 121° C. and 20 min. Medium C was prepared as another medium by sterilizing 1000 L of a medium (medium B: glucose monohydrate 112 kg) under conditions of 140° C. for 40 sec and adding the sterilized medium to the above medium A. pH of medium C was measured and found to be pH 6.1. The seed culture (second stage) solution was then inoculated into medium C, and the volume was adjusted to an initial amount of culture solution of 5600 L in total (volume of culture tank: 10 kL). Culture was started under conditions of temperature 26° C., air flow rate 49 $Nm^3$/hr, and inner pressure 200 kPa. The form of the culture tank was such that six-blade turbines were provided in two stages and the ratio of the diameter of the agitation impeller (=d) to the inner diameter of the tank (=D) was d/D=0.34. Foaming during culture was detected with an antifoaming sensor, and a soybean oil was automatically added to prevent the culture solution from being discharged from the tank by foaming. While feeding a medium as shown in Table 9, main culture was carried out for 288 hr. At the end of the culture, the amount of the culture solution was 7,600 L due to the influence of an increase in amount of the solution by the feed of the medium and a decrease in amount of the solution by evaporation of the solution.

For condition (7-2), main culture was carried out in the same manner as in condition (7-1), except that medium A was adjusted to pH 4.5 by nonaseptic addition of sulfuric acid, medium C was adjusted to pH 6.1 by aseptic addition of an aqueous sodium hydroxide solution, and a culture tank of d/D=0.3 was used. For condition (7-3), culture was carried out in the same manner as in condition (7-1), except that a culture tank of d/D=0.30 was used. For condition (7-4), culture was carried out in the same manner as in condition (7-1), except that a culture tank of d/D=0.25 was used. The concentration of dihomo-γ-linolenic acid produced per liter of the culture solution at the end of the culture was 12.3 g/L for both condition (7-1) and condition (7-2), was 11.0 g/L for condition (7-3), and was 10.0 g/L for condition (7-4).

TABLE 9

Medium feeding in Example 7

| Main culture time | Medium fed |
|---|---|
| After 19 hours | glucose monohydrate 280 kg/460 L |
| After 43 hours | glucose monohydrate 280 kg/450 L |
| After 67 hours | glucose monohydrate 280 kg/450 L |
| After 120 hours | glucose monohydrate 336 kg/530 L |

After the completion of the culture, the culture solution was sterilized under conditions of 120° C. for 20 min. Wet cells were then collected by a continuous dehydrator. The collected wet cells were dried in a vibration fluidized bed dryer to a water content of 1% by weight. The dried cells were transported by an air transport machine to a filling place and, together with nitrogen gas, were filled into a container bag of an aluminum pouch having a volume of about 1 $m^3$. The mouth part of the bag was heat sealed, and the container bag was then stored in a refrigerator of 10° C. or below.

The dried cells were taken out of the container bag and were subjected to extraction with hexane. The solid matter was removed from the hexane solution by filtration. The filtrate was then heated under reduced pressure to remove hexane to give a crude oil comprising dihomo-γ-linolenic acid as a constituent fatty acid. The crude oil was analyzed, and the results of the analysis are shown in Table 10. For the culture tank of d/D=0.34, the crude oil had an ester-type sterol content of not more than 1%. For the culture tank of d/D=0.3, the pH adjustment under condition (7-3) by the conventional method provided a crude oil having a high ester-type sterol content. Sterilization of the medium nitrogen source at pH 4.5 as in condition (7-2) lowered the ester-type sterol content to not more than 1%. For the culture tank of d/D=0.25, the ester-type sterol content exceeded 1%.

TABLE 10

Found values for dihomo-γ-linolenic acid-containing crude oil

| Example or control example | Example 7 Condition 7-1 | Example 7 Condition 7-2 | Example 7 Condition 7-3 (control example) | Example 7 Condition 7-4 (control example) |
|---|---|---|---|---|
| Form of culture tank, d/D | 0.34 | 0.30 | 0.30 | 0.25 |
| Adjusted pH value of medium A (before sterilization) | 6.1 | 4.5 | 6.1 | 6.1 |
| pH value of medium C (after sterilization and before inoculation of seed culture solution) | 6.1 | 6.1 | 6.1 | 6.1 |
| Wt % of each fraction | | | | |
| Triglyceride | 93.8% | 94.1% | 93.5% | 93.0% |
| Unsaponifiable matter | 2.1% | 2.2% | 2.9% | 2.9% |
| Ester-type sterol | 0.9% | 1.0% | 1.2% | 1.2% |
| Dihomo-γ-linolenic acid in total fatty acid in crude oil, % | 42.2% | 41.9% | 40.7% | 41.7% |

Example 8

Production of Dihomo-γ-Linolenic Acid; Culture Under Concentration of Soy Flour 1.5%

*Moltierella alpina* (SAM 1860) was provided, and seed culture was carried out in the same manner as in Example 7. Next, 4500 L of a medium (medium A: soy flour 84 kg, $KH_2PO_4$ 16.8 kg, $MgCl_2.6H_2O$ 2.8 kg, $CaCl_2-2H_2O$ 2.8 kg, soybean oil 5.6 kg) was sterilized under conditions of 121° C. and 20 min. Medium C was prepared as another medium by sterilizing 1000 L of a medium (medium B: glucose monohydrate 112 kg) under conditions of 140° C. for 40 sec and adding the sterilized medium to the above medium A. Medium C was adjusted to pH 6.1, and the seed culture solution was then inoculated into medium C, and the volume was adjusted to an initial amount of culture solution of 5600 L in total (volume of culture tank: 10 kL).

Culture was started under conditions of temperature 26° C., air flow rate 49 $Nm^3$/hr, and inner pressure 200 kPa. Regarding the form of the culture tank, a culture tank provided with six-blade turbines of d/D (the ratio of the diameter of the agitation impeller (=d) to the inner diameter of the tank (=D))=0.34 in two stages and a culture tank provided with six-blade turbines of d/D=0.25 in two stages were used. Foaming during culture was detected with an antifoaming sensor, and a soybean oil was automatically added to prevent the culture solution from being discharged from the tank by foaming. While feeding a medium as shown in Table 11, main culture was carried out for 162 hr. At the end of the culture, the concentration of dihomo-γ-linolenic acid produced per liter of the culture solution was 4.8 g/L for the tank of d/D=0.34 and was 4.7 g/L for the tank of d/D=0.25.

TABLE 11

Medium feeding in Example 8

| Main culture time | Medium fed |
|---|---|
| After 19 hours | glucose monohydrate 84 kg/200 L |
| After 43 hours | glucose monohydrate 84 kg/200 L |
| After 67 hours | glucose monohydrate 84 kg/120 L |
| After 91 hours | glucose monohydrate 84 kg/125 L |

After the completion of the culture, in the same manner as in Example 7, dried cells were collected, followed by extraction with hexane to give a crude oil comprising dihomo-γ-linolenic acid as a constituent fatty acid. The crude oil was analyzed, and the found values for the crude oil are shown in Table 12.

TABLE 12

Results of Example 8 (found values for dihomo-γ-linolenic acid-containing crude oil)

| Form of culture tank, d/D | 0.25 | 0.34 |
|---|---|---|
| Wt % of each fraction | | |
| Triglyceride | 93.5% | 93.0% |
| Unsaponifiable matter | 1.2% | 1.2% |
| Ester-type sterol | 0.4% | 0.4% |
| Dihomo-γ-linolenic acid in total fatty acid in crude oil, % | 40.5% | 41.3% |

Example 9

Production of Mead Acid: d/D 0.5, Concentration of Soy Flour in Medium 4%

The present inventors have established a production process of a fat or oil (triglyceride) comprising a ω9 highly unsaturated fatty acid as a constituent fatty acid. The fat or oil can be produced by culturing microorganisms having ω9 highly unsaturated fatty acid producing capability, for example, a mutant *Moltierella alpina* (SAM 1861) strain (FERM P-3590) according to the production process described in Japanese Unexamined Patent Publication (Kokai) No. 5 (1993)-91888.

The present inventors have also established a production process of a fat or oil (triglyceride) comprising a Mead acid as a constituent fatty acid. This fat or oil is produced by subjecting a microorganism capable of producing arachidonic acid to mutation treatment according to the method described in Japanese Unexamined Patent Publication (Kokai) No. 10 (1998)-57085. The fat or oil can be produced by culturing a mutant strain having lowered or deleted Δ12 desaturase and at least one enhanced activity of Δ5 desaturation activity, Δ6 desaturation activity and/or chain extension activity, for example, *Moltierella alpina* (SAM 2086) (FERM P-15766).

*Mortierella alpina* (SAM 2086) was provided as a Mead acid-producing fungus. A standard strain of *Mortierella*

*alpina* was inoculated into a medium (1% yeast extract, 2% glucose, pH 6.3) in an amount of 500 mL contained in a 2000 mL Erlenmeyer flask. Seed culture (first stage) was started under conditions of reciprocating shaking 100 rpm and temperature 28° C., and the seed culture was continued for 3 days. Next, 30 L of a medium (1% yeast extract, 2% glucose, 0.1% olive oil, pH 6.3) was prepared in a 50 L-volume aeration-agitation culture tank. The seed culture (first stage) solution was inoculated into the medium. Seed culture (second stage) was started under conditions of agitation speed 300 rpm, temperature 28° C., and inner pressure of tank 200 kPa, and the seed culture was continued for 2 days. Next, 3200 L of a medium (medium A: soy flour 160 kg, olive oil 4 kg) was sterilized at 121° C. for 20 min.

Medium C was prepared as another medium by sterilizing 700 L of a medium (medium B: glucose monohydrate 80 kg) under conditions of 140° C. for 90 sec and adding the sterilized medium to the above medium A. Medium C was adjusted to pH 6.1, and seed culture (second stage) solution was then inoculated into medium C, and the volume was adjusted to an initial amount of culture solution of 4000 L in total (volume of culture tank: 10 kL). Main culture was started under conditions of temperature 24° C., air flow rate 49 Nm$^3$/hr, inner pressure 200 kPa, and agitation power requirement 2 kW. On the 4th day of the culture, the temperature was changed to 20° C. Regarding the form of the culture tank, a culture tank provided with six-blade turbines of d/D (the ratio of the diameter of the agitation impeller (=d) to the inner diameter of the tank (=D))=0.5 in two stages was used. While feeding a medium as shown in Table 13, main culture was carried out for 456 hr. At the end of the culture, the concentration of Mead acid produced per liter of the culture solution was 10.1 g/L.

TABLE 13

Medium feeding in Example 9

| Main culture time | Medium fed |
|---|---|
| After 19 hours | glucose monohydrate 160 kg/280 L |
| After 43 hours | glucose monohydrate 160 kg/280 L |
| After 67 hours | glucose monohydrate 120 kg/210 L |
| After 91 hours | glucose monohydrate 120 kg/210 L |
| After 144 hours | glucose monohydrate 80 kg/140 L |

After the completion of the culture, the culture solution was sterilized under conditions of 120° C. for 20 min. Wet cells were then collected by a continuous dehydrator. The collected wet cells were dried in a vibration fluidized bed dryer to a water content of 1% by weight. The dried cells, together with nitrogen gas, were filled into a filling-type container bag by an air transport machine. The mouth part of the bag was heat sealed, and the container bag was then stored, in a refrigerator, at 10° C. or below.

The dried cells were taken out of the container bag and were subjected to extraction with hexane. The solid matter was removed from the hexane solution by filtration. The filtrate was then heated under reduced pressure to remove hexane to give a Mead acid-containing crude oil. The crude oil was analyzed, and the results are shown in Table 14.

Example 10

Production of Mead Acid, d/D=0.25, Concentration of Soy Flour in Medium=4%

Seed culture was carried out in the same manner as in Example 9. Main culture was carried out under the same conditions as in Example 9, except that, regarding the form of the culture tank, a tank provided with six-blade turbines of d/D=0.25 in two stages was used. As a result, the concentration of Mead acid produced per liter of the culture solution at the end of the culture was 8.0 g/L. After the completion of the culture, a crude oil comprising Mead acid as a constituent fatty acid was obtained in the same manner as in Example 9.

The Mead acid-containing crude oil was analyzed, and the found values for the crude oil are shown in Table 14.

TABLE 14

Found values for Mead acid-containing crude oil

| Example or control example | Example 9 | Example 10 (Control example) |
|---|---|---|
| Form of culture tank, d/D | 0.5 | 0.25 |
| Wt % of each fraction | | |
| Triglyceride | 94.6% | 93.0% |
| Unsaponifiable matter | 1.8% | 2.8% |
| Ester-type sterol | 0.6% | 1.2% |
| Mead acid in total fatty acid in crude oil, % | 35.0% | 30.6% |

Example 11

Production of Mead Acid, Culture Under Condition of Soy Flour Concentration=1.5%

*Mortierella alpina* (SAM 2086) was provided, and seed culture was carried out in the same manner as in Example 9. Next, 3200 L of a medium (medium A: soy flour 60 kg, olive oil 4 kg) was sterilized under conditions of 121° C. for 20 min. Medium C was prepared as another medium by sterilizing 700 L of a medium (medium B: glucose monohydrate 80 kg) under conditions of 140° C. for 90 sec and adding the sterilized medium to the above medium A. Medium C was adjusted to pH 6.1, and seed culture solution was then inoculated into medium C, and the volume was adjusted to an initial amount of culture solution of 4000 L in total (volume of culture tank: 10 kL). Main culture was started under conditions of temperature 24° C., air flow rate 49 Nm$^3$/hr, inner pressure 200 kPa, and agitation power requirement 2 kW.

On the 4th day of the culture, the temperature was changed to 20° C. Regarding the form of the culture tank, a culture tank provided with six-blade turbines of d/D (the ratio of the diameter of the agitation impeller (=d) to the inner diameter of the tank (=D))=0.34 in two stages and a culture tank provided with six-blade turbines of d/D=0.25 in two stages were used. While feeding a medium as shown in Table 15, main culture was carried out for 300 hr. At the end of the culture, the concentration of Mead acid produced per liter of the culture solution was 3.9 g/L for the tank of d/D=0.34 and was 3.8 g/L for the tank of d/D=0.25.

TABLE 15

Medium feeding in Example 11

| Main culture time | Medium fed |
|---|---|
| After 19 hours | glucose monohydrate 60 kg/120 L |
| After 43 hours | glucose monohydrate 60 kg/120 L |
| After 67 hours | glucose monohydrate 40 kg/80 L |
| After 91 hours | glucose monohydrate 40 kg/80 L |

After the completion of the culture, in the same manner as in Example 9, dried cells were collected, followed by extraction with hexane to give a crude oil comprising Mead acid as a constituent fatty acid. The crude oil was analyzed, and the found values for the crude oil are shown in Table 16.

TABLE 16

Results of Example 11 (found values for Mead acid-containing crude oil)

| Form of culture tank, d/D | 0.25 | 0.34 |
|---|---|---|
| Wt % of each fraction | | |
| Triglyceride | 95.0% | 95.1% |
| Unsaponifiable matter | 1.3% | 1.3% |
| Ester-type sterol | 0.5% | 0.5% |
| Mead acid in total fatty acid in crude oil, % | 34.5% | 34.2% |

Example 12

Preparation of Capsule Blended with Refined Fat or Oil (Triglyceride) Comprising Arachidonic Acid as Constituent Fatty Acid and Having Lowered Ester-Type Sterol Content Water was added to 100 parts by weight of gelatin and 35 parts by weight of edible glycerin, and the mixture was heated at 50 to 60° C. for dissolution to prepare a gelatin film. Next, a mixture of the refined fat or oil 5-A (triglyceride) having lowered ester-type sterol content and comprising arachidonic acid as a constituent fatty acid prepared in Example 5 with 0.05% of a vitamin E oil was provided as contents of capsules. Capsule forming and drying were carried out by a conventional method to prepare soft capsules containing 180 mg of contents per capsule. Soft capsules were also prepared using the refined fat or oil 5-B, prepared in Example 5, as a raw material in the same manner as in the preparation of capsules using the refined fat or oil 5-A.

Example 13

Use in Fatty Transfusion Preparation 400 g of the refined fat or oil 5-A (triglyceride) having lowered ester-type sterol content and comprising arachidonic acid as a constituent fatty acid prepared in Example 5, 48 g of refined egg-yolk lecithin, 20 g of oleic acid, 100 g of glycerin, and 40 ml of 0.1 N caustic soda were added and dispersed in a homogenizer. Distilled water for injections was then added to the dispersion to bring the volume of the dispersion to 4 liters, followed by emulsification with a high-pressure atomization emulsifying machine to prepare a lipid emulsion. 200 ml aliquots of the lipid emulsion were dispensed into plastic bags, and high-pressure steam sterilization was then carried out at 121° C. for 20 min to prepare fatty transfusion preparations. Further, a fatty transfusion preparation using the refined fat or oil 5-B prepared in Example 5 as a raw material was prepared in the same manner as in the preparation of the fatty transfusion preparation using the refined fat or oil 5-A.

Example 14

Use in Juice 2 g of β-cyclodextrin was added to 20 ml of a 20% aqueous ethanol solution. 100 mg of the refined fat or oil 5-A (triglyceride), prepared in Example 5, having lowered ester-type sterol content and comprising arachidonic acid as a constituent fatty acid (blended with 0.05% of vitamin E) was added thereto with stirring by means of a stirrer, and the mixture was incubated at 50° C. for 2 hr. After cooling to room temperature (about one hr), the mixture was incubated at 4° C. for additional 10 hr with stirring.

The resultant precipitate was collected by centrifugation, was washed with n-hexane, and then lyophilized to give 1.8 g of a cyclodextrin inclusion compound containing arachidonic acid-containing triglyceride. 1 g of this powder was homogeneously mixed into 10 L of juice to prepare juice containing a refined fat or oil (triglyceride) having lowered ester-type sterol content and comprising arachidonic acid as a constituent fatty acid. Juice using the refined fat or oil 5-B prepared in Example 5 as a raw material was also prepared in the same manner as in the preparation of the juice using the refined fat or oil 5-A.

Example 15

Use in Powdered Milk 0.3 g of the refined fat or oil 5-A (triglyceride), prepared in Example 5, having lowered ester-type sterol content and comprising arachidonic acid as a constituent fatty acid was mixed into 100 g of powdered milk to prepare formula powder. Further, formula powder using the refined fat or oil 5-B prepared in Example 5 as a raw material was also prepared in the same manner as in the preparation of the formula powder using the refined fat or oil 5-A.

Example 16

Culture Method Using Various Strains

*Mortierella elongata* (IFO 8570), *Mortierella hygrophila* (IFO 5941), *Echinosporangium transversale* (NRRL 3116), *Conidiobolus nanodes* (CBS 154.56), and *Saprolegnia lapponica* (CBS 284.38) were used as arachidonic acid producing fugi. Standard strains of these arachidonic acid producing fugi were inoculated into a medium (yeast extract 1%, glucose 2%, pH 6.3), and seed culture was carried out for 3 days under conditions of reciprocating shaking 100 rpm and temperature 28° C.

Next, 25 L of a medium (glucose 500 g, soy flour 775 g, $KH_2PO_4$ 50 g, $MgCl_2.6H_2O$ 7.5 g, $CaCl_2.2H_2O$ 7.5 g, and soybean oil 25 g, pH 6.3) was prepared in a 50 L-volume aeration-agitation culture tank. The seed culture solution was inoculated into the medium, and main culture was started under conditions of agitation speed of 200 rpm, temperature 28° C., and tank inner pressure 150 kPa. Regarding the form of the culture tank, a culture tank provided with six-blade turbines of d/D=0.42 in two stages was used. The culture was carried out for 186 hr while adding a 50% glucose solution at about 24-hr intervals so as to bring the glucose concentration to about 1 to 2%.

After the completion of the culture, the culture solution was sterilized under conditions of 120° C. and 20 min. Wet cells were collected by filtration under reduced pressure and were dried to a water content of 1% by weight. The dried cells were extracted with hexane. The solid matter was removed from the hexane solution by filtration. The filtrate was then heated under reduced pressure to remove hexane to give a crude oil comprising arachidonic acid as a constituent fatty acid. The arachidonic acid-containing crude oil was analyzed. Found values for the crude oil are shown in Table 17.

TABLE 17

Results of Example 16 (found values for arachidonic acid-containing crude oil)

| Strain | M. elongata IFO 8570 | M. hygrophila IFO 5941 | E. transversale NRRL 3116 | C. nanodes CBS 154.56 | S. lapponica CBS 284.38 |
|---|---|---|---|---|---|
| Wt % of each fraction | | | | | |
| Triglyceride | 90.0% | 88.1% | 86.0% | 83.4% | 82.6% |
| Unsaponifiable matter | 1.9% | 1.9% | 2.0% | 2.0% | 2.0% |
| Ester-type sterol | 0.8% | 0.7% | 0.7% | 0.8% | 0.8% |
| Arachidonic acid in total fatty acid in crude oil, % | 30.8% | 31.7% | 28.6% | 26.3% | 20.7% |

The invention claimed is:

1. A process for producing a crude oil having lowered unsaponifiable matter content and/or ester-type sterol content and a highly unsaturated fatty acid as a constituent fatty acid, comprising obtaining a microorganism capable of producing a fat or oil comprising an unsaturated fatty acid as a constituent fatty acid and culturing the microorganism in a medium containing a nitrogen source concentration of 2 to 15% within a culture tank equipped with an agitation impeller satisfying the requirement that the ratio of the diameter of agitation impeller (=d) to the inner diameter of the culture tank (=D) is d/D=0.30 to 0.6.

2. The process according to claim 1, wherein the ratio of the diameter of agitation impeller (=d) to the inner diameter of the culture tank (=D) is d/D=0.34 to 0.6.

3. The process according to claim 1, wherein the nitrogen source contains a nitrogen source which has been sterilized at a pH of not more than 5.

4. The process according to claim 1 further comprising a step of refining the crude.

5. The process according to claim 1, wherein not less than 70% of the fat or oil comprising said highly unsaturated fatty acid as the constituent fatty acid is accounted for by a triglyceride.

6. The process according to claim 1, wherein the highly unsaturated fatty acid constituting the fat or oil is γ-linolenic acid (18:3 ω6), dihomo-γ-linolenic acid (20:3 6), arachidonic acid (20:4 ω6), 7,10,13,16-docosatetraenoic acid (22:4 ω6), 4,7,10,13,16-docosapentaenoic acid (22:5 ω6), α-linolenic acid (18:3 ω3), 6,9,12,15-octadecatetraenoic acid (18:4 ω3), 8,11,14,17-eicosatetraenoic acid (20:4 ω3), eicosapentaenoic acid (20:5 ω3), 7,10,13,16,19-docosapentaenoic acid (22:5 ω3), 4,7,10,13,16,19-docosahexaenoic acid (22:6 ω3), 6,9-octadecadienoic acid (18:2 ω9), 8,11-eicosadienoic acid (20:2 ω9), or 5,8,11-eicosatrienoic acid (Mead acid: 20:3 ω9) or a combination of two or more of them.

7. The process according to claim 1, wherein the microorganism is one belonging to the genus *Mortierella, Conidiobolus, Pythium, Phytophthora, Penicillium, Cladosporium, Mucor, Fusarium, Aspergillus, Rhodotorula, Entomophthora, Echinosporangium*, or *Saprolegnia*.

8. The process according to claim 1, wherein said microorganism is one belonging to the genus *Mortierella*, subgenus *Mortierella*.

9. The process according to claim 8, wherein the microorganism belonging to the subgenus *Mortierella* is the species *alpina* belonging to the genus *Mortierella*.

10. A crude oil comprising a fat or oil having lowered unsaponifiable matter content and/or ester-type sterol content comprising, as a constituent fatty acid, a highly unsaturated fatty acid, wherein the ester-type sterol content of the fat or oil is 0.8% by weight or less; said highly unsaturated fatty acid content is 30% by weight or more; and the content of triglyceride is 90% by weight or more based on the total fatty acid in the fat or oil.

11. A therapeutic nutrition food comprising the crude oil of claim 10 and/or the refined fat or oil obtained by refining the crude oil.

12. A food for animals or fishes, comprising the crude oil of claim 10 and/or the refined fat or oil obtained by refining the crude oil.

13. A pharmaceutical composition, comprising the crude oil of claim 10 and/or the refined fat or oil obtained by refining the crude oil.

14. A pharmaceutical composition prepared by using the crude oil of claim 10 and/or the refined fat or oil obtained by refining the crude oil.

15. The process according to claim 4, wherein not less than 70% of the fat or oil comprising said highly unsaturated fatty acid as the constituent fatty acid is accounted for by a triglyceride.

16. The therapeutic nutrition food according to claim 11, further comprising a neutral carrier suitable for oral, intrarectal or parenteral administration.

17. A general food and drink, a functional food, a nutrition supplement, a formula for premature babies, a formula for mature babies, a food for infants, a food for expectant and nursing mothers, or a food for aged persons, comprising the crude oil and/or the refined fat or oil according to claim 10.

18. A refined oil comprising a fat or oil having lowered unsaponifiable matter content and/or ester-type sterol content comprising, as a constituent fatty acid, a highly unsaturated fatty acid, wherein the ester-type sterol content of the fat or oil is 0.8% by weight or less; said highly unsaturated fatty acid content is 30% by weight or more; and the content of triglyceride is 90% by weight or more based on the total fatty acid in the fat or oil.

19. The crude oil according to claim 10, wherein the content of triglyceride is 94% by weight or more.

20. The crude oil according to claim 18, wherein the content of triglyceride is 94% by weight or more.

* * * * *